United States Patent [19]

Okaniwa et al.

[11] 4,427,632

[45] Jan. 24, 1984

[54] ANALYTICAL ELEMENT

[75] Inventors: Kenichiro Okaniwa; Mikio Koyama; Shozo Kikugawa, all of Hino, Japan

[73] Assignee: Konishiroku Photo Industry Co., Ltd., Tokyo, Japan

[21] Appl. No.: 370,854

[22] Filed: Apr. 22, 1982

[30] Foreign Application Priority Data

Apr. 29, 1981 [JP] Japan ................................ 56-65446

[51] Int. Cl.$^3$ ...................... G01N 33/52; G01N 33/66
[52] U.S. Cl. ........................................ 422/56; 422/57; 435/14
[58] Field of Search .................................... 422/56, 57

[56] References Cited

U.S. PATENT DOCUMENTS 3,992,158 11/1976 Przybylowicz ...................... 422/57
4,292,272 9/1981 Kitajima ........................... 422/56 X
4,356,149 10/1982 Kitajima ........................... 422/57 X Primary Examiner—Sidney Marantz
Attorney, Agent, or Firm—Frishauf, Holtz, Goodman & Woodward

[57] ABSTRACT

An analytical element which comprises (a) a light-transmissive and liquid-impermeable support, (b) at least one reagent layer containing at least one reagent reactive with a component in a liquid sample and being constituted of a hydrophilic colloid, and (c) at least one developing layer of a fibrous structure being positioned on said reagent layer on the side opposite to said support for permitting the component in said liquid sample to permeate therethrough toward said reagent layer and having been formed by coating said reagent layer with a dispersion comprising an organic macromolecular polymer having reactive groups and a fibrous material.

17 Claims, No Drawings

ANALYTICAL ELEMENT

This invention relates generally to analytical chemistry, particularly to an analytical element for analysis of a predetermined specific component in a liquid. More particularly, it pertains to a quantitative analytical element for assay of a specific component in a biological liquid sample.

There have been developed a great number of methods for analysis of components in liquid samples. For example, there may be mentioned automatic quantitative analytical devices. These are frequently used and very useful especially in clinical test laboratories in hospitals and the like. Such automatic analytical devices employ techniques based on continuous system analysis, in which samples, diluents and analytical reagents are mixed together and conveyed to analytical devices, as disclosed in, for example, U.S. Pat. No. 2,797,149.

Such continuous automatic analytical devices, however, are complicated and expensive, requiring skilled operators. In addition, repeated washing operations required to be performed after the analytical operations will consume much time as well as labor, and the wastewaters resulting from these operations will disadvantageously involve the problem of causing environmental pollution.

On the other hand, as contrasted to the analytical system employing solutions as mentioned above, there is another analytical system employing dry chemistry. These are called as test papers or test strips and provided in the dry form, prepared by dipping an absorptive carrier such as a filter paper in an analytical reagent solution followed by drying, as disclosed in, for example, U.S. Pat. No. 3,050,373 or U.S. Pat. No. 3,061,523. The test strip enables measurement by dipping in a liquid sample of analyte and then withdrawing to read the color change or density change on the test strip with the naked eye or by means of an instrument such as densitometer.

These test strips are easy in handling and useful in giving instantly the test results. But, these test strips comprising reagents carried in absorptive carriers suffer from various vital defects, and therefore their applications are still limited to qualitative or semi-quantitative analysis.

For overcoming these defects, there has been developed an analytical element as disclosed in U.S. Pat. No. 3,992,158. These elements have a reagent layer containing analytical reagents and a spreading layer comprising an isotropically porous, non-fibrous medium laminated on a transparent support.

The developing layer disclosed in said Patent, however, has essentially only brittle strength. A high percentage of these films tend to break making it difficult to maintain a stable supply. Also, from aspects of preparation, it is required to control severely the conditions for coating, and constant void volume (porosity) can hardly be obtained if such conditions are not satisfied.

The object of the present invention is to provide an analytical element having excellent quantitative characteristics without requiring skilled operational techniques.

The present inventors have made extensive studies and were successful in overcoming the drawbacks as mentioned above by use of an analytical element having the following constitution.

That is, the analytical element according to the present invention comprises a light-transmissive and liquid-impermeable support, at least one reagent layer containing at least one reagent reactive with a component in a liquid sample and being constituted of a hydrophilic colloid, and at least one developing layer having a fibrous structure positioned on the opposite side of said support to said reagent layer for permitting the component in said liquid sample to permeate therethrough to said reagent layer, said developing layer being formed by coating a dispersion comprising an organic macromolecular polymer having reactive groups and a fibrous material.

In the following, the analytical element according to the present invention is described in further detail.

First, the aforesaid liquid-impermeable and light-transmissive support of the analytical element according to the present invention (hereinafter abbreviated as the support according to the present invention) is not particularly limited, so long as it is impermeable to liquid and can transmit light. For example, various polymeric materials such as cellulose acetates, polyethyleneterephthalates, polycarbonates or polystyrenes are suitable for this purpose of use. The above support employed may have any desired thickness, but preferably a thickness of about 50 microns to 250 microns. It is also possible to work freely one side of the support according to the present invention, which is the side for observation, depending on the intended purpose. When the aforesaid reagent layer according to the present invention is provided directly on the above support, it may directly be coated thereon. In some cases, adhesion between the reagent layer and the support may effectively be enhanced by application of a light-transmissive undercoating layer on the support.

The above reagent layer according to the present invention contains reagents which carry out quantitative reactions with analytes to be analyzed in said layer, and it is used to permit the quantitative reactions to proceed within said layer.

The above reagent layer contains a hydrophilic colloid as a medium and is formed as a layer by being coated on a support. With such a constitution, as different from the prior art in which a carrier such as a filter paper is impregnated with reagents, reagents can be evenly contained in the layer, with an additional advantage that the content of reagents can freely be controlled. As a hydrophilic colloidal substance to be used in such a reagent layer according to the present invention, a natural or synthetic macromolecular substance is preferred. More preferably, there may be included gelatins, gelatin derivatives such as modified gelatins, polyvinyl alcohols, polyvinyl pyrrolidones, etc. Among them, a particularly preferred hydrophilic colloidal substance is a gelatin derivative such as gelatin.

These hydrophilic colloidal substances preferably have a swelling degree of about 150 to 500%, and its film thickness, which can be selected as desired, is required to be at least about 5 microns.

The reagents to be contained in the reagent layer formed as described above will of course be determined depending on the analytes to be analyzed in samples as well as on the analytical reaction selected for analysis of said analytes. When the analytical reaction selected is constituted of two or more reagents, these reagents may be contained by mixing together in the same reagent layer or alternatively contained in two or more separate layers. These constitutions may freely be selected so long as no detrimental effect is caused, partly because they are sometimes determined depending on the mechanism of the analytical reaction per se.

On the other hand, it is possible to carry out the analytical reactions of two or more analytes in a sample in the same reagent layer. In this case, it is necessary to select the two or more kinds of analytical reactions so that they may not interfere with each other or have no influence on each other in measurement of the reaction products produced.

The thus constituted reagent layer can generally be coated on the support according to the present invention in a manner of a coating, but, as mentioned above, there may also be provided various layers between the reagent layer and the support except for those which are not suitable for the purpose of the present invention.

The developing layer of a fibrous structure according to the present invention is provided either as a single layer or a plurality of layers directly or indirectly on the reagent layer which has been previously provided on the support as described above.

The developing layer of a fibrous structure is provided for the purposes mentioned below:

(1) to uniformly distribute a predetermined volume of a liquid sample at a ratio of a constant volume per unit area in the reagent layer;

(2) to remove substances or factors which interfere with the analytical reactions in the liquid sample; and (3) to perform background action to reflect the light to be measured transmitted through the support in carrying out, for example, spectro-photometric analysis.

Thus, the fibrous developing layer according to the present invention can perform all of the three functions as mentioned above, but the three functions can also conveniently be separated into different layer according to the functions.

Further, it is also possible to use a combination of a layer having two of the three functions and a layer having the other remaining function.

The fibrous developing layer according to the present invention as described above may have a film thickness, which can freely be selected depending on the purpose, but preferably about 30 microns to about 600 microns, more preferably about 50 microns to about 400 microns.

And, the fibrous developing layer according to the present invention, as distinguished from the reticulate or fabric structure as disclosed in Japanese Patent Publication No. 6551/1978 or Japanese Provisional Patent Publication No. 164356/1980, has of course a free pore area which is substantially zero.

As the materials for forming the fibrous developing layer according to the present invention, there may be included natural celluloses or derivatives thereof, synthetic fibers such as polyethylenes, polypropylenes, polyamides and others, said layers including those constituted of various fibers, irrespective of whether they are synthetic or natural, which are randomly three-dimensionally intertwined with each other.

Further, as the materials for forming the above fibrous developing layer, there may be chosen either single species or plural species with any desired grain size, generally of 50 mesh to 325 mesh according to the JIS standard screen, preferably 100 to 320 mesh, more preferably 200 to 300 mesh.

The organic macromolecular polymer having reactive groups according to the present invention markedly enhances the film strength in the above fibrous developing layer through said reactive groups and also the adhesion strength through chemical bonding of said reactive groups with the layer beneath said layer maintains its appearance and structure against external physical force.

The organic macromolecular polymer according to the present invention may have one or two or more kinds of reactive groups. If desired, heating or a catalyst may be employed for effecting chemical bonding between the reactive groups. The organic macromolecular polymer having reactive groups can be prepared, for example, by homopolymerization or copolymerization of monomers having reactive groups or precursors thereof. The macromolecular organic polymer having two or more kinds of reactive groups can be prepared, for example, by copolymerization of monomers having different kinds of reactive groups or precursors thereof. When monomers having precursors of the reactive groups are employed, they can be converted to organic macromolecular polymers having the reactive groups, for example, after formation of the organic macromolecular polymers, by treatment such as hydrolysis. In the present invention, the monomer unit having a reactive group may be contained in an amount of preferably about 0.1 to about 30% by weight based on said organic macromolecular polymer unit, particularly 0.5 to 20%.

As the monomers having the reactive groups as described above, there may be mentioned monomers having epoxy groups, monomers having aziridyl groups, monomers having formyl groups, monomers having hydroxymethyl groups, monomers having isocyanate groups, monomers having thiol groups and monomers having carbamoyl groups.

As a monomers having an epoxy group, there may be mentioned, for example, glycidyl acrylate, glycidyl methacrylate, allyl glycidyl ether, 4-vinylcyclohexane monoepoxide, etc. A monomer having an aziridyl group may be exemplified by aziridylethyl methacrylate, 1-ethylenesulfonyl aziridine, 1-ethylenecarbonyl aziridine, aziridylethyl acrylate, etc. Typical examples of a monomer having a formyl group are acrolein and methacrolein. A monomer having a hydroxymethyl group may include, for example, N-methylol-acrylamide, N-methylol-methacrylamide, N-methylol-diacetoneacrylamide, and the like. Typical examples of a monomer having an isocyanate group are vinyl isocyanate and allyl isocyanate. Examples of a monomer having a thiol group are vinyl thiol, p-thiol styrene, m-thiol styrene, vinyl benzyl thiol and acetyl derivatives of these. As a monomer having a carbamoyl group, there may be included, for example, acrylamide, methacrylamide, maleinamide, diacetone acrylamide, etc.

As other monomers to be copolymerized with the monomers having reactive groups, there may be selected any monomer, so long as the resultant organic macromolecular polymer satisfies the conditions of liquid impermeability and non-swellability.

Among the monomers having various reactive groups as mentioned above, typical examples of the monomers having an epoxy group, aziridyl group, hydroxylmethyl group or carbamoyl group may be inclusive of those mentioned hereinabove. Examples of monomers having other reactive groups are as follows. As a monomer having carboxyl group, there may be mentioned acrylic acid, methacrylic acid, itaconic acid, maleic acid, itaconic acid half-ester, maleic acid half-ester, etc. A monomer having an amino group may be exemplified by aminostyrene, N,N-dimethylaminoethyl acrylate, N,N-dimethylaminoethyl methacrylate. Typical examples of a monomer having a methoxy group are methoxyethyl acrylate, ethoxyethyl acrylate, methoxyethyl methacrylate, ethoxyethyl methacrylate, and the like. As a monomer having —COOC$_4$H$_9$(t) group, there may be included tert-butyl acrylate, tert-butyl methacrylate. Examples of a monomer having a ureido group are ureidoethyl acrylate, ureidoethyl methacrylate, ureidovinyl ether (e.g., those represented by the formula CH$_2$=CHONRCONHR', wherein R represents a hydrogen atom or a methyl and R' a hydrogen atom or a lower alkyl such as methyl or ethyl). As a monomer having a hydroxyl group, there may be mentioned 2-hydroxyethyl acrylate, 2-hydroxyethyl methacrylate, 2-hydroxypropyl methacrylate, 2-hydroxypropyl acrylate, etc. A monomer having a haloethylsulfonyl group may be exemplified by chloroethylsulfonylethyl methacrylate, bromoethylsulfonylethyl methacrylate, etc. A typical example of a monomer having a vinylsulfonyl group is vinylsulfonylethyl methacrylate. Examples of a monomer having an active methylene containing group are acryloyl acetone and methacryloyl acetone. As a monomer having a carboxymethoxymethyl group, there may be mentioned, for example, N-carboxymethoxymethyl-acrylamide and N-carboxymethoxymethyl-methacrylamide.

Examples of other preferable monomers to be copolymerized with the monomers having reactive groups as described above are set forth below.

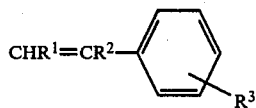

(I)

wherein each of $R^1$ and $R^2$, which can be the same or different, represents a non-interfering substituent such as a hydrogen atom, a halogen atom, or a substituted or unsubstituted, amino-free alkyl or aryl group having 1 to 10 carbon atoms and $R^3$ represents a hydrogen atom, a halogen atom, or a substituted or unsubstituted, amino-free aliphatic or aromatic group having 1 to 10 carbon atoms. As aliphatic or aromatic groups, there may be included alkyl groups, alkoxy groups, aryl groups and aryloxy groups. Typical examples of the monomers represented by the formula (I) are styrene, vinyltoluene, vinylbenzyl chloride, t-butylstyrene, etc.

(II)

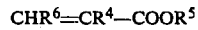

CHR$^6$=CR$^4$—COOR$^5$ wherein $R^6$ has the same meaning as $R^1$ in the formula (I), $R^4$ represents a hydrogen atom or a methyl and $R^5$ represents an aryl, an alkyl, an alkaryl or aralkyl group, each having 1 to 10 carbon atoms.

(III) Polymerizable unsaturated nitrile monomers such as acrylonitrile and methacrylonitrile.

(IV) Interparticle crosslinking monomers having two addition-polymerizable groups such as divinylbenzene, N,N-methylene-bis(acrylamide), ethylene diacrylate and ethylene dimethacrylate.

By copolymerization of a suitable combination of these monomers with the aforesaid monomers having reactive groups, it is possible to constitute the polymer particle units according to the present invention. The monomers of formulae (I), (II) and (III) may be contained in amounts of 0 to 99.5% by weight based on said organic macromolecular polymer units; and the monomer represented by formula (IV) may be contained in an amount of 0 to 10% by weight, preferably 0 to 5% by weight based on said organic macromolecular polymer unit.

Among the organic macromolecular polymers according to the present invention, typical examples of those having one kind of reactive group are shown below, by which the present invention is not limited. The numerals in the brackets affixed to each exemplary compound indicate the weight percents of monomers employed in polymerization.

EXEMPLARY COMPOUNDS (1-1) Poly(styrene-co-glycidyl methacrylate) [90/10]
(1-2) Poly(styrene-co-methyl acrylate-co-glycidyl methacrylate) [80/15/5]
(1-3) Poly(styrene-co-n-butyl methacrylate-co-glycidiyl methacrylate) [75/15/10]
(1-4) Poly(styrene-co-vinylbenzyl chloride-co-glycidyl methacrylate) [80/10/10]
(1-5) Poly(styrene-co-divinylbenzene-co-glycidyl acylate) [90/2/8]
(1-6) Poly(p-vinyltoluene-co-glycidyl methacrylate) [90/10]
(1-7) Poly(methylmethacrylate-co-glycidyl methacrylate) [80/20]
(1-8) Poly(styrene-co-N,N-dimethylaminoethyl methacrylate) [95/5]
(1-9) Poly(styrene-co-aziridylethyl methacrylate) [95/5]
(1-10) Poly(styrene-co-methyl acrylate-co-acrolein) [90/5/5]
(1-11) Poly(styrene-co-acrylamide) [95/5]
(1-12) Poly(styrene-co-vinylthiol) [95/5]
(1-13) Poly(styrene-co-methylolacrylamide) [95/5]
(1-14) Poly(styrene-co-t-butylacrylate-co-glycidyl methacrylate) [90/5/5]
(1-15) Poly(styrene-co-vinylisocyanate) [95/5]
(1-16) Poly(methylacrylate-co-styrene-co-N-methylolacrylamide) [50/35/15]
(1-17) Poly(styrene-co-N,N-dimethylaminoethyl methacrylate) [90/10]
(1-18) Poly(styrene-co-acrylic acid) [97/3]
(1-19) Poly(styrene-co-acrylamide) [97/3]
(1-20) Poly(p-vinyltoluene-co-tert-butyl acrylate) [95/5]
(1-21) Poly(methyl acrylate-co-methacrylamide) [95/5]
(1-22) Poly(styrene-co-N-methylol acrylamide) [95/5]
(1-23) Poly(p-vinylbenzylchloride-co-N-methylol acrylamide) [96/4]
(1-24) Poly(styrene-co-itaconic acid) [98/2]
(1-25) Poly(styrene-co-tert-butyl acrylate) [92/8]
(1-26) Poly(methyl acrylate-co-styrene-co-acrolein) [30/65/5]
(1-27) Poly(methyl methacrylate-co-styrene-co-2-hydroxyethyl methacrylate) [25/70/5]
(1-28) Poly(styrene-co-vinylsulfonylethyl acrylate) [80/20]
(1-29) Poly(styrene-co-N,N-diethylaminomethyl acrylate) [97.5/2.5]
(1-30) Poly(styrene-co-methyl acrylate-co-acetoacetoxyethyl acrylate) [90/5/5]
(1-31) Poly(styrene-co-methacrylic acid) [95/5]

Further, as another embodiment of the present invention, examples of organic macromolecular polymers containing two or more kinds of monomer units having different reactive groups are shown below, by which the present invention is not limited.

EXEMPLARY COMPOUNDS (2-1) Poly(styrene-co-glycidyl methacrylate-co-N,N-dimethylaminoethyl methacrylate) [90/5/5]
(2-2) Poly(styrene-co-methacrylic acid-co-acrylamide) [95/2/3]
(2-3) Poly(styrene-co-N-methylol acrylamide-co-methoxyethyl acrylate) [90/5/5]
(2-4) Poly(p-vinyltoluene-co-N-methylol acrylamide-co-acrylic acid) [90/8/2]
(2-5) Poly(methyl methacrylate-co-glycidyl methacrylate-co-t-butyl acrylate) [80/10/10]
(2-6) Poly(styrene-co-p-vinylbenzyl chloride-co-acrylic acid-co-ethyl acrylate) [75/10/5/10]
(2-7) Poly(styrene-co-methacrolein-co-2-hydroxyethyl methacrylate) [90/5/5]
(2-8) Poly(styrene-co-acrolein-co-acetoacetoxyethyl methacrylate) [85/5/10]
(2-9) Poly(styrene-co-N,N-dimethylaminoethyl acrylate-co-vinylsulfonylethyl methacrylate) [90/5/5]
(2-10) Poly(p-vinyltoluene-co-aminostyrene-co-vinylsulfonylethyl methacrylate) [85/10/5]

The above organic macromolecular polymer containing these reactive groups can be produced by various conventional polymerization methods.

Typical addition polymerization methods may include solution polymerization (appropriate precipitation operation and, in some cases, crushing and particle classification operations are used for formation of said heat-stable particle units), suspension polymerization (sometimes referred to as pearl polymerization), emulsion polymerization, dispersion polymerization and precipitation polymerization. Preferably, suspension polymerization and emulsion polymerization are employed.

In the following, Synthetic examples of the exemplary compounds of the present invention are shown, but the present invention is not limited thereby.

SYNTHESIS EXAMPLE 1

Synthesis of the exemplary compound (1-1)

A mixture of monomers and a polymerization initiator comprising 90 parts of styrene, 10 parts of glycidyl methacrylate, and 3 parts of 2,2'-azobis(2,4-dimethylvaleronitrile) was added into 700 ml of an aqueous solution of 3% by weight of tricalcium phosphate and 0.04% by weight of sodium dodecylbenzene sulfonate based on the above monomers, while stirring the mixture at a stirring speed of 5000 r.p.m. by means of a TK-homojetter (produced by Tokushu Kika Kogyo). After completion of the addition, the mixture was further continued to be stirred for about 30 minutes until the particle size became about 20 microns as observed by a microscope, whereupon the mixture was transferred into a four-necked flask equipped with a conventional stirrer (anchor type), a cooling tube, a nitrogen gas inlet tube and a thermometer. The stirring speed was changed to 200 r.p.m., and polymerization was carried out at 60° C. under a nitrogen gas stream for 8 hours to complete the reaction. Then, the contents were cooled to room temperature and tricalcium phosphate was removed by decomposition with a dilute aqueous hydrochloric acid solution. The residual mixture was washed repeatedly with water and thereafter the polymer was separated by filtration, followed by drying, to obtain the polymer of the exemplary compound (1-1).

SYNTHESIS EXAMPLE 2

Synthesis of the exemplary compound (1-1)

Into a 1000 ml four-necked flask equipped with a thermometer, a stirring means, a cooling tube and a nitrogen inlet tube, there were changed 500 ml of degassed distilled water, 5 ml of Trax H-45 (trade name, surfactant, produced by Nippon Oil and Fat Co., Ltd., effective ingredient 30%), 135 g of styrene and 15 g of glycidyl methacrylate, and the mixture was stirred at a stirring speed of 50 r.p.m. while under the flows of nitrogen and cooling water. Then, the inner temperature in the flask was elevated to 60° C., and aqueous solutions of 1.3 g of potassium persulfate and 0.865 g of sodium metabisulfite each dissolved in 20 ml of degassed water were added at the same time. The reaction was carried out for 6 hours while maintaining the stirring speed at 250 r.p.m. and the inner temperature in the flask at 60° C. Then, the reaction mixture was cooled to room temperature and the reaction product filtered to give a latex of the exemplary compound (1-1) having a viscosity of 5.5 cps (measured by B-type viscometer) with a solid content of 20%.

SYNTHESIS EXAMPLE 3

Synthesis of the exemplary compound (1-3)

A mixture of monomers and a polymerization initiator comprising 75 parts of styrene, 15 parts of n-butyl methacrylate, 10 parts of glycidyl methacrylate and 3 parts of 2,2'-azobis(2,4-dimethylvaleronitrile) was added to 700 ml of an aqueous solution of 2% by weight of tricalcium phosphate and 0.02% by weight of sodium dodecylbenzene sulfonate based on the above monomers, while stirring the mixture at a stirring speed of 2000 r.p.m. by means of a TK-homojetter. After completion of the addition, the mixture was further continued to be stirred for 30 minutes until the particle sizes of the droplets of the monomer mixture became about 100 microns, whereupon the reaction and the procedures as described in Synthetic example 1 were repeated, to provide the polymer of the exemplary compound (1-3).

The above organic macromolecular polymer containing the reactive groups according to the present invention have a glass transition temperature (hereinafer abbreviated as $T_g$), typically of 30° C. or higher, preferably a $T_g$ of 40° C. or higher. The term "$T_g$" mentioned in the present specification means a temperature at which the polymer undergoes change in state from a glassy state to a rubbery state, and may be contemplated as an index for heat stability of the polymer. The $T_g$ of a polymer can be measured according to the method as described in, for example, "Techniques and Methods of Polymer Evaluation" Vol. 1, Marcel Dekker, Inc., N.Y. (1966).

Various methods can be employed in applying said organic macromolecular polymer in the above dispersion for forming the fibrous developing layer of the present invention. For example, said organic macromolecular polymer may be dissolved in the above dispersion, or alternatively said organic macromolecular polymer may preferably be dispersed in a liquid carrier which does not dissolve said polymer (e.g. in the form of fine powders or a latex).

The above organic macromolecular polymer may be used in an amount which can widely be selected, but preferably in an amount such that a substantial portion of the interstitial volume formed by three-dimensional intertwining of fibers may not be filled therewith, namely 50% by weight to 0.005% by weight, preferably 30% by weight to 0.05% by weight based on the weight of fibers.

Further, either one kind or two or more kinds of the above organic macromolecular polymer may be employed and it is also useful to use a hydrophilic collodial substance as described above in combination.

The fibrous developing layer of the present invention can be prepared by coating according various methods. As an example, the following steps may be mentioned. That is, the fibers of the present invention are dispersed in a liquid carrier which does not dissolve said fibers, then the organic macromolecular polymer having reactive groups as described above is added thereto to prepare a dispersion of said fibers, and after application of the stable dispersion onto a support, the liquid carrier is removed while forming said fibrous structure.

A dispersion useful for preparation of the fibrous developing layer is required to be stable during a time sufficient to apply the dispersion onto a support.

To form such stable dispersions, a wide variety of techniques can be used individually or in combination. One useful technique comprises the addition of a surfactant to the liquid carrier to facilitate distribution and stabilization of the fibers in the dispersion.

Representative surfactants which can be employed include Triton®X-100 (octylphenoxy polyethoxyethanol from Rohm and Hass) and Surfactant 10G® (nonylphenoxy polyglycidol from Olin Corp.).

The above surfactant may be employed in an amount which can be selected from a wide range, but generally 30% by weight to 0.005% by weight, preferably 20% by weight to 0.05% by weight, based on the weight of the fibrous material. As alternative techniques, there are procedures such as sonication treatments, physical blending and agitation treatments and pH adjustments. These techniques can be more useful when combined with the technique as described above.

As the liquid carrier in the aforesaid dispersion, there may be employed an aqueous liquid. But other liquid carriers such as organic liquids may also be available, provided that said fibers are insoluble in the carrier so that their fibrous structural character can be retained.

Representative liquid carriers other than water may include water-miscible organic solvents, mixtures of water with water-miscible organic solvents and appropriate water-immiscible organic solvents. Examples of water-miscible organic solvents are lower alcohols (namely, alcohols with alkyl groups having 1 to 4 carbon atoms), acetone and tetrahydrofuran. As the water-immiscible solvents, there may be mentioned lower alkyl esters such as ethyl acetate, halogenated organic solvents such as halogenated hydrocarbons (e.g., chloroform, methylene chloride and carbon tetrachloride), and hydrocarbon solvents such as aromatic hydrocarbons (e.g. benzene, toluene and xylene) and aliphatic hydrocarbons (e.g. hexane, decalin, etc.).

The analytical elements according to the present invention containing the aforesaid fibrous developing layer can have any one of a variety of different configurations. It may have one or more of the fibrous developing layers of the present invention, or alternatively a suitable combination of the fibrous developing layer with any of a variety of functional layer, reagent containing layers and members, as exemplified by the reagent layer, the filtration layer, the reflection layer and the subbing layer as disclosed in U.S. Pat. No. 3,992,158, the radiation-blocking layer as disclosed in U.S. Pat. No. 4,042,335, the barrier layer as disclosed in U.S. Pat. No. 4,066,403, the registration layer as disclosed in U.S. Pat. No. 4,144,306, the migration-inhibition layer as disclosed in U.S. Pat. No. 4,166,093, the scintillation layer as disclosed in U.S. Pat. No. 4,127,499, the scavenger layer as disclosed in Japanese Provisional Patent Publication No. 90859/1980 and the destructive pad-shaped member as disclosed in U.S. Pat. No. 4,110,079, to constitute the analytical element adapted to accommodate the object of the present invention.

Further, the analytical element having the fibrous developing layer according to the present invention can be subjected to the so called "calendering treatment" by passing through a pair of pressure rollers thereby to increase the flatness of the surface of said developing layer and obtain more favorable effect in optical reflection.

The analytical element of the present invention having the constitution as described above can accomplish its object by supplying a liquid sample through the fibrous developing layer and observing the analytical reaction in the reagent layer from the side of the transparent support.

The amount of a liquid sample to be applied to the analytical element of the present invention can be determined as desired, but preferably in the range of from about 50 $\mu$l to about 5 $\mu$l, more preferably from about 20 $\mu$l to about 5 $\mu$l. Usually, about 10 $\mu$l of a liquid sample is preferably used.

The analytical reaction to be used for the analytical element of the present invention may optionally be determined depending on the intended purpose. For example, it may be employed for analysis of a biological liquid sample, namely for analysis of components in blood or urine.

These can easily be constituted by suitable selection of the analytical reagents so as to be available for analysis of, for example, glucose, urea nitrogen, ammonia, uric acid, cholesterol triglyceride, creatine, creatinine, bilirubin as well as many other components.

The analytical element having the fibrous developing layer of this invention can be coated by the dip coating method, the air knife method, the curtain coating method or the extrusion coating method with the use of a hopper as disclosed in U.S. Pat. No. 2,681,294. If desired, it is also possible to use the method as disclosed in U.S. Pat. No. 2,761,791 and U.K. Pat. No. 837,095 for simultaneous coating of two or more layers.

Elements of the present invention can be adapted for use not only in the field of clinical chemistry, but in other fields of chemical analysis. In addition, by utilizing the function of holding a certain amount of liquid within a certain area of the film, the element of the present invention can be associated with other functional layers (e.g., layers of photographic elements).

Analytical elements of the present invention are very advantageous for use in clinical testing of body fluids, such as blood, blood serum, lymph and urine. In particular, blood serum is conventionally used in analysis of blood. But the analytical element can be conveniently applicable for analysis of any of whole blood, blood serum and blood plasma.

When whole blood is used, a radiation-blocking layer or other reflecting layer may be provided, if necessary, in order to avoid interference of detecting radiation by the blood cells. Of course, if it is desired to observe directly the color of blood cells directly, such as in a haemoglobin analysis, no such reflecting layer is necessary.

After the analytical result is obtained as a detectable change, by use of the analytical element of the present invention, it is measured by reflection spectrophotometry, transmission spectrophotometry, fluorescence spectrophotometry or scintillation counting, corresponding the various detectable changes. The thus obtained values of measurement can be utilized for determination of the unknown quantity of analyte with reference to the calibration curve previously prepared.

Also, by utilization of the reactive groups possessed by the organic macromolecular polymer contained in the fibrous developing layer of the present invention, application of the present analytical element for immunoassay is possible.

The analytical element of the present invention, having the constitution as described in detail above, is substantially free from generation of irregular concentrations of reagents or chromatographic phenomenon, and therefore it can be used for quantitative analysis of a liquid sample, especially components in a biological liquid sample, easily and rapidly by means of a conventional spectrophotometer.

Further, formation of a fibrous developing layer in the analytical element of the present invention can be effected by simple coating and drying thereof, under the conditions of coating and drying which are not specifically limited, to a practical advantage of very easy preparation.

The present invention is illustrated in further detail by referring to the following Examples, by which the present invention is not limited at all.

EXAMPLE 1

On a transparent poly(ethyleneterephthalate) support of a film thickness of about 180 microns, there was coated 216 mg/dm$^2$ of deionized gelatin to a thickness of about 20 microns of dried film. On the above gelatin layer, there were further coated the fibrous dispersions having the compositions as shown in Table 1 to form Samples 1, 2, 3, 4, 5 and 6, respectively.

adhered on a transparent poly(ethyleneterephthalate) support with a thickness of 180 μm to provide Comparative sample (I), and the same filter paper after impregnated with 5% aqueous gelatin solution followed by drying was adhered directly on the same support to provide Comparative sample (II).

On these Samples 1, 2, 3, 4, 5, 6 and Comparative samples (I) and (II), 10 μl of an aqueous solution of a red dye Brilliant Scarlet 3R was added dropwise, and 7 minutes later, spot diameters were measured from the side of the support.

Also, reflection density (by Sakura Photoelectric Densitometer PAD-60 Model, produced by Konishiroku Photo Industry Co., Ltd.) was measured from the side of the support using a green ($\lambda_{max}$=546 nm) filter to determine the difference ΔD between the maximum density and the minimum density within the spot. Measurements were conducted ten times for each Sample and each Comparative sample to determine an average value, maximum and minimum values of spot diameter and also the maximum ΔD within the ten measurements.

The results are given in the following Table 2.

TABLE 2

| | Spot diameter (mm) | | | |
|---|---|---|---|---|
| | Maximum | Minimum | Average | ΔD |
| Comparative sample (I) | 16.1 | 10.3 | 13.3 | 0.21 |
| Comparative sample (II) | 16.4 | 9.1 | 12.7 | 0.24 |
| Sample of the invention (1) | 10.5 | 10.0 | 10.1 | 0.02 |
| Sample of the invention (2) | 10.1 | 10.0 | 10.0 | 0.01 |
| Sample of the invention (3) | 11.1 | 10.5 | 11.1 | 0.04 |
| Sample of the invention (4) | 10.1 | 10.0 | 10.1 | 0.02 |
| Sample of the invention (5) | 10.2 | 10.1 | 10.2 | 0.03 |
| Sample of the invention (6) | 10.1 | 10.0 | 10.1 | 0.02 |

TABLE 1

| | Fibrous dispersion | | | | |
|---|---|---|---|---|---|
| Sample No. | Dispersion No. | Fiber | Liquid carrier | Organic polymer | Surfactant |
| Sample-1 | Dispersion-1 | F-1, 5 g | Xylene, 14 ml | Exemplary compound (1-1) *(1) 0.75 g | G 0.5 g |
| Sample-2 | Dispersion-2 | F-1, 5g | Toluene, 15 ml | Exemplary compound (1-12) *(1) 0.5 g | H 0.2 g |
| Sample-3 | Dispersion-3 | F-1, 5 g | Acetone, 14 ml | Exemplary compound (2-1) *(1) 0.25 g | G 0.3 g |
| Sample-4 | Dispersion-4 | F-2, 5 g | Xylene, 19 ml | Exemplary compound (1-10) *(1) 0.5 g | — |
| Sample-5 | Dispersion-5 | F-1, 5 g | Water *(2), 20 ml | Exemplary compound (1-1) *(2) 0.3 g | G 0.4 g |
| Sample-6 | Dispersion-6 | F-1, 5 g | Water *(2), 20 ml | Exemplary compound (2-1) *(2) 0.5 g | G 0.4 g |

In the above Table:
F-1 is filter paper powder C (produced by Toyo Roshi);
F-2 is filter paper powder A (produced by Toyo Roshi);
G is octylphenoxypolyethoxyethanol;
H is nonylphenoxyglycidol.
*(1) used as a solution
*(2) used as a 15% latex/water dispersion On the other hand, as a comparative sample, a filter paper (No. 7 produced by Toyo Roshi Co.) was directly As shown in the above Table 2, the Samples of the present invention vary little in spot diameter and the density distribution in the coloring region is very small.

On the other hand, in Comparative samples, spot diameters are greatly varied. In addition, the density is also greatly varied within the coloring region.

EXAMPLE 2

On a transparent poly(ethyleneterephthalate) support having a thickness of 180 microns which had been subjected to undercoating, a reagent layer for assay of glucose comprising the following composition was coated:

A reagent layer for assay of glucose, containing the following components, adjusted with 5% aqueous sodium hydroxide solution to pH 7.0:

| Glucose oxidase | 240 U/dm$^2$ |
|---|---|
| 4-Aminoantipyrine hydrochloride | 0.0086 g/dm$^2$ |
| 1,7-Dihydroxynaphthalene | 0.0065 g/dm$^2$ |
| Peroxidase | 180 U/dm$^2$ |
| 5,5-Dimethyl-1,3-cyclohexadione | 0.0022 g/dm$^2$ |
| 6-Amino-4,5-dihydroxy-2-methyl pyrimidine | 0.0002 g/dm$^2$ |
| 3,3-Dimethylglutaric acid | 0.0196 g/dm$^2$ |
| Deionized gelatin | 0.196 g/dm$^2$ |

On the above reagent layer, the dispersion-I of Example 1 was coated and dried to prepare Sample-7, and similarly the dispersion-6 of Example 1 coated and dried to prepare Sample-8. On these analytical elements, there were added dropwise aqueous solutions of various concentrations of 100 mg/dl, 150 mg/dl, 200 mg/dl, 250 mg/dl, 300 mg/dl, 350 mg/dl and artificial serum containing equal amounts of glucose. After incubation at 37° C. for 7 minutes, the densities of reddish brown dye formed were measured at wavelength of 490 nm, whereby it was found that the glucose density was proportional to the reflection density.

We claim:

1. An analytical element for determining the presence of a component in a liquid sample comprising:
   (a) a light-transmissive and liquid-impermeable support;
   (b) at least one reagent layer containing at least one reagent reactive with said component and containing a hydrophilic colloid; and
   (c) at least one hydrophobic developing layer having a fibrous structure and being positioned on the side of said reagent layer opposite to said support whereby the component in said liquid sample permeates through said developing layer toward said reagent layer, said developing layer formed by coating said reagent layer with a homogeneous dispersion comprising a hydrophobic organic macromolecular polymer having reactive groups and a fibrous material.

2. The analytical element of claim 1, wherein said dispersion contains said hydrophobic organic macromolecular polymer having reactive groups in an amount of 0.005 to 50% by weight based on said fibrous material.

3. The analytical element of claim 1, wherein said reactive groups of the hydrophobic organic macromolecular polymer are selected from the group consisting of epoxy, aziridyl, formyl, hydroxymethyl, isocyanate, thiol and carbamoyl groups.

4. The analytical element of claim 1, wherein said fibrous material for the developing layer is selected from the group consisting of natural celluloses, natural cellulose derivatives, polyethylenes, polypropylenes and polyamides.

5. The analytical element of claim 1, wherein said developing layer has a thickness of 30 to 600 microns.

6. The analytical element of claim 1, wherein said dispersion contains at least one surfactant.

7. The analytical element of claim 6, wherein said dispersion contains said surfactant in an amount of 0.005 to 30% by weight based on said fibrous material.

8. The analytical element of claim 1, wherein said support has a thickness of about 50 to 250 microns.

9. The analytical element of claim 8, wherein said support comprises a compound selected from cellulose acetates, polyethyleneterephthalates, polycarbonates and polystyrenes.

10. The analytical element of claim 1, wherein said hydrophilic colloid is selected from the group consisting of gelatins, gelatin derivatives, polyvinyl alcohols and polyvinyl pyrrolidones.

11. The analytical element of claim 10, wherein said hydrophilic colloid is gelatin.

12. The analytical element of claim 10, wherein said hydrophilic colloid has a film thickness of at least about 5 microns.

13. The analytical element of claim 1, wherein said hydrophobic organic macromolecular polymer consists essentially of a copolymer having at least one monomer having reactive groups and at least one monomer selected from the group consisting of:

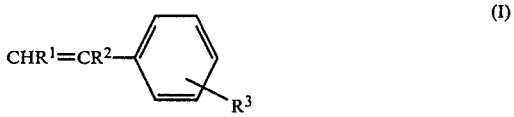

(I)

wherein each of R$^1$ and R$^2$, which can be the same or different, is a non-interfering substituent selected from a hydrogen atom, a halogen atom, and a substituted or unsubstituted amino-free alkyl or aryl group having 1 to 10 carbon atoms and R$^3$ is selected from a hydrogen atom, a halogen atom, or a substituted or unsubstituted, amino-free aliphatic or aromatic group having 1 to 10 carbon atoms;

(II)

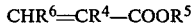

wherein R$^6$ has the same meaning as R$^1$ in formula (I), R$^4$ is selected from the group consisting of a hydrogen atom and a methyl group and R$^5$ is selected from the group consisting of an aryl, an alkyl, an alkaryl and aralkyl group, each having 1 to 10 carbon atoms;

(III) polymerizable unsaturated nitrile monomers; and (IV) interparticle crosslinking monomers having two addition-polymerizable groups.

14. The analytical element of claim 13, wherein the copolymer is comprised of 0.1 to 30% by weight of the monomer having reactive groups, 0 to 99.5% by weight of the monomer (I), 0 to 99.5% by weight of the monomer (II), 0 to 99.5% by weight of the monomer (III) and 0 to 10% by weight of the monomer (IV).

15. The analytical element of claim 13, wherein the monomer having reactive groups is present in an amount of 0.1 to 30% by weight based on said hydrophobic organic macromolecular polymer.

16. The analytical element of claim 15, wherein the monomer having reactive groups is present in an amount of 0.5 to 20% by weight based on said hydrophobic organic macromolecular polymer.

17. An analytical element for determining the presence of a component in a liquid sample comprising:
   (a) a light-transmissive and liquid-impermeable support selected from cellulose acetates, polyethyleneterephthalates, polycarbonates and polystyrenes;
   (b) at least one reagent layer containing at least one reagent reactive with said component and containing a hydrophilic colloid selected from the group consisting of gelatins, gelatin derivatives, polyvinyl alcohols and polyvinyl pyrrolidones, said hydrophilic colloid having a film thickness of at least about 5 microns; and
   (c) at least one hydrophobic developing layer having a fibrous structure and being positioned on the side of said reagent layer opposite to said support whereby the component in said liquid sample permeates through said developing layer toward said reagent layer, said developing layer formed by coating said reagent layer with a homogeneous dispersion comprising a hydrophobic organic macromolecular polymer having reactive groups and a fibrous material, said hydrophobic organic macromolecular polymer consisting essentially of a copolymer having at least one monomer having reactive groups and at least one monomer selected from the group consisting of:

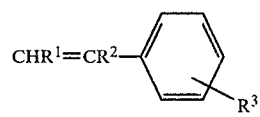

(I)

wherein each of $R^1$ and $R^2$, which can be the same or different, is a non-interfering substituent selected from a hydrogen atom, a halogen atom, and a substituted or unsubstituted amino-free alkyl or aryl group having 1 to 10 carbon atoms and $R^3$ is selected from a hydrogen atom, a halogen atom, or a substituted or unsubstituted, amino-free aliphatic or aromatic group having 1 to 10 carbon atoms;

(II)

$CHR^6=CR^4-COOR^5$ wherein $R^6$ has the same meaning as $R^1$ in formula (I), $R^4$ is selected from the group consisting of a hydrogen atom and a methyl group and $R^5$ is selected from the group consisting of an aryl, an alkyl, an alkaryl and aralkyl group, each having 1 to 10 carbon atoms;

(III) polymerizable unsaturated nitrile monomers; and (IV) interparticle crosslinking monomers having two addition-polymerizable groups, wherein the monomer having reactive groups is present in an amount of 0.1 to 30% by weight based on said hydrophobic organic macromolecular polymer.

* * * * *